(12) United States Patent
Pryor et al.

(10) Patent No.: US 8,088,175 B2
(45) Date of Patent: Jan. 3, 2012

(54) ALL NATURAL HAIR COLORING AGENT

(76) Inventors: Paula Pryor, Torrence, CA (US); Marc Pryor, Torrence, CA (US)

( * ) Notice: Subject to any disclaimer, the term of this patent is extended or adjusted under 35 U.S.C. 154(b) by 0 days.

(21) Appl. No.: 12/932,229

(22) Filed: Feb. 22, 2011

(65) Prior Publication Data

US 2011/0203056 A1  Aug. 25, 2011

Related U.S. Application Data

(60) Provisional application No. 61/306,611, filed on Feb. 22, 2010.

(51) Int. Cl.
 *A61Q 5/10* (2006.01)

(52) U.S. Cl. ............. 8/405; 8/406; 8/435; 8/611; 8/646
(58) Field of Classification Search ............. 8/405, 406, 8/435, 611, 646
See application file for complete search history.

(56) References Cited

U.S. PATENT DOCUMENTS 6,398,822 B1 * 6/2002 Brock et al. ............... 8/428

* cited by examiner

*Primary Examiner* — Eisa Elhilo
(74) *Attorney, Agent, or Firm* — Robert M. Sperry

(57) ABSTRACT

Improved hair coloring agents which do not adversely effect the health of the user and which are environmentally safe and which permanently colors only gray hair.

13 Claims, 1 Drawing Sheet

PREFERRED FORMUILA FOR HAIR COLORING AGENT

Water ................................. 44.455%

Alcohol .............................. 44.455%

Glycerin ........................... .09%

Dihydroxyacetone ............. 10.00%

Herbs ................................. 1.00%

PREFERRED FORMUILA FOR HAIR COLORING AGENT

| | |
|---|---|
| Water | 44.455% |
| Alcohol | 44.455% |
| Glycerin | .09% |
| Dihydroxyacetone | 10.00% |
| Herbs | 1.00% |

FIG. 1

ALL NATURAL HAIR COLORING AGENT

RELATED CASES

This invention is described in my Provisional Patent Application, Ser. No. 61/306,611 filed Feb. 22, 2010, and now Feb. 17, 2011.

FIELD OF INVENTION

This invention relates to hair coloring and is particularly directed to improved hair coloring agents which do not contain harmful ingredients, such as lead, peroxide, ammonia and the like.

BACKGROUND

Many people wish to cover gray hair because of premature graying or to look younger for personal or professional reasons. However, most prior art hair coloring agents use ingredients, such as lead, peroxide, ammonia and the like, which can adversely effect the user's health and are unsafe for the environment. Hence, some people resort to wigs or other means to hide their gray hair. Unfortunately, these alternatives are expensive and often look silly or are unsuccessful in satisfactorily hiding the user's gray hair. Moreover, some coloring agents only provide temporary coloring and, hence, must be reapplied frequently. Thus, none of the prior art means for covering gray hair have been entirely satisfactory.

BRIEF SUMMARY AND OBJECTS OF INVENTION

These disadvantages of the prior art are overcome with the present invention and improved hair coloring agents are provided which quickly, effectively and permanently color gray hair, yet which are environmentally safe and which do not adversely effect the health of the user.

These advantages of the present invention are preferably attained by providing improved hair coloring agents which employ dihydroxyacetone as the active ingredient which permanently colors gray hair while not effecting other hair color.

Accordingly, it is an object of the present invention to provide improved hair coloring agents.

An additional object of the present invention is to provide improved hair coloring agents which permanently color gray hair.

Another object of the present invention is to provide improved hair coloring agents which do not adversely effect the health of the user.

A further object of the present invention is to provide improved hair coloring agents which do not adversely effect the health of the user and which are environmentally safe.

An additional object of the present invention is to provide improved hair coloring agents which do not adversely effect the health of the user and which are environmentally safe, yet which quickly serve to permanently color gray hair.

Another object of the present invention is to provide improved hair coloring agents which do not adversely effect the health of the user and which are environmentally safe, yet which quickly and effectively serve to permanently color gray hair.

A further object of the present invention is to provide improved hair coloring agents which do not adversely effect the health of the user and which are environmentally safe, yet which quickly and effectively serve to permanently color gray hair, while not effecting other hair color.

A specific object of the present invention is to provide improved hair coloring agents using dihydroxyacetone as the active agent, which permanently colors gray hair while not effecting other hair color.

These and other objects and features of the present invention will be apparent from the following detailed description, taken with reference to the figures of the accompanying drawing.

BRIEF DESCRIPTION OF THE DRAWING

FIG. 1 is a formula for the hair coloring agent of the present invention.

DETAILED DESCRIPTION OF THE INVENTION

In that form of the present invention chosen for purposes of illustration, FIG. 1 shows a preferred formula for the hair coloring agent of the present invention. As seen in FIG. 1, the preferred formula calls for 44.455% Water, 44.455% Alcohol, 0.09% Glycerin, 10%, Dihydroxyacetone, and 1% herbs. It is found that this formulation provides a hair coloring agent which quickly and permanently colors gray hair, yet which does not effect the color of other hair and is completely safe for both the user and the environment. Obviously, some variation of the ingredients can be made and it has been found the the following ranges are acceptable. Water 25-40%, Alcohol 30-40% Dihydroxyacetone 5-30%, preservative, 1-5% and herbs 1-5%.

In use, the user should wash their hair and spray on the hair coloring agent of the present invention daily for three days or until the desired hair color density is obtained. The gray hairs will gradually become colorized and, after the third day will have achieved a permanent subtle brownish tint. Subsequently, the hair coloring agent can be reapplied as needed to cover hair growth.

Obviously, numerous variations and modifications can be made without departing from the spirit of the present invention which permanently colors gray hair while not effecting other hair color. Therefore, it should be clearly understood that the forms of the present invention described above and shown in the accompanying drawing are illustrative only and are not intended to limit the scope of the present invention.

What is claimed is:

1. A hair coloring agent comprising:
   Water 25-40%, Alcohol 30-40%, Dihydroxyacetone 5-30%, glycerin 1-5%, preservative 1-5% and 1-5% herbs.
2. The hair coloring agent of claim 1 wherein:
   said hair coloring agent is safe for the user.
3. The hair coloring agent of claim 1 wherein:
   said hair coloring agent is safe for the environment.
4. The hair coloring agent of claim 1 wherein:
   said hair coloring agent gradually colors gray hair over a period of three days.
5. A hair coloring agent consisting of:
   Water 44.455%, Alcohol 44.455%, Glycerin 0.09%, Dihydroxyace-tone 10% and Herbs 1%.
6. The method of coloring gray hair comprising the steps of:
   applying hair coloring agent as defined in claim 5.
7. The method of claim 6 wherein:
   said applying step is repeated daily.
8. The method of claim 7 wherein:
   said applying is repeated daily for three days.

9. The method of claim 8 wherein:
after said three days, said hair coloring agent is applied as needed.
10. The method of claim 6 wherein:
said method is repeated as needed.
11. The hair coloring agent of claim 1 wherein:
said hair coloring agent permanently colors the hair.

12. The hair coloring agent of claim 11 wherein:
said hair coloring agent colors only gray hair.
13. The method of claim 6 wherein:
said method is repeated until the desired color density is achieved.

* * * * *